United States Patent [19]

Wehner et al.

[11] Patent Number: 5,030,671
[45] Date of Patent: Jul. 9, 1991

[54] MERCAPTOBENZOATES AS STABILIZERS FOR CHLORINE-CONTAINING POLYMERS

[75] Inventors: Wolfgang Wehner, Zwingenberg; Gerd Abeler, Darmstadt, both of Fed. Rep. of Germany

[73] Assignee: Ciba-Geigy Corporation, Ardsley, N.Y.

[21] Appl. No.: 421,575

[22] Filed: Oct. 16, 1989

[30] Foreign Application Priority Data

Oct. 20, 1988 [CH] Switzerland ............... 3912/88

[51] Int. Cl.$^5$ ............ C07C 321/26; C07D 251/34; C08K 5/37
[52] U.S. Cl. ............ 524/101; 524/289; 524/392; 524/393; 544/222; 560/15; 560/17; 560/18
[58] Field of Search .......... 524/101, 289, 392, 393; 544/222; 560/15, 17, 18; 521/89, 117, 121, 90

[56] References Cited

U.S. PATENT DOCUMENTS

| | | | |
|---|---|---|---|
| 3,067,166 | 12/1962 | Zaremsky | 524/289 |
| 3,144,422 | 8/1964 | Homberg | 524/302 |
| 3,242,133 | 3/1966 | Lindsey | 524/392 |
| 4,336,168 | 6/1982 | Hoch et al. | 524/302 |
| 4,361,665 | 11/1982 | Miller et al. | 524/302 |
| 4,647,629 | 3/1987 | Michel et al. | 525/274 |

FOREIGN PATENT DOCUMENTS

| | | |
|---|---|---|
| 1631 | 5/1979 | European Pat. Off. |
| 39159 | 11/1981 | European Pat. Off. |
| 133130 | 2/1985 | European Pat. Off. |
| 321405 | 12/1988 | European Pat. Off. |
| 1217609 | 5/1966 | Fed. Rep. of Germany |
| 936770 | 9/1963 | United Kingdom |

*Primary Examiner*—Veronica P. Hoke
*Attorney, Agent, or Firm*—JoAnn Villamizar

[57] ABSTRACT

A composition containing a) a chlorine-containing polymer, b) at least one Me(II) carboxylate and/or Me(II) phenolate, wherein Me(II) represents Ba, Ca, Mg, Sr or Zn, and c) at least one compound of formula I

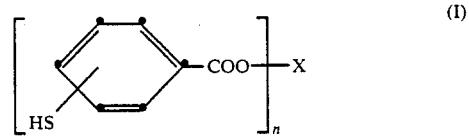

wherein n is 1, 2, 3, 4 or 6 and, when n is 1, X is $C_1$-$C_{20}$alkyl, $C_3$-$C_{20}$-alkenyl, $C_5$-$C_{12}$cycloalkyl, $C_5$-$C_{12}$cycloalkyl substituted by $C_1$-$C_4$alkyl, phenyl, $C_7$-$C_9$phenylalkyl, phenyl substituted by from 1 to 3 radicals or $C_7$-$C_9$phenylalkyl substituted on the phenyl ring by from 1 to 3 radicals, the radicals being selected from the group consisting of $C_1$-$C_4$alkyl, chlorine, hydroxy, methoxy and ethoxy; when n is 2, X is $C_2$-$C_{12}$alkylene, $C_2$-$C_{12}$alkylene substituted by phenyl, or $C_2$-$C_{12}$alkylene interrupted by oxygen or sulfur atoms; when n is 3, X is, for example, $C_3$-$C_7$alkanetriyl; when n is 4, X is, for example, $C_4$-$C_{10}$alkanetetrayl, and when n is 6, X is a group of formula IV

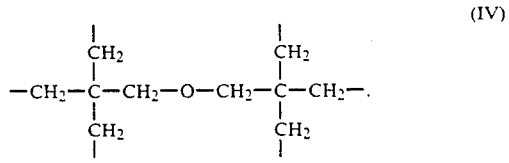

Some of the compounds of formula I are novel.

13 Claims, No Drawings

MERCAPTOBENZOATES AS STABILIZERS FOR CHLORINE-CONTAINING POLYMERS

The present invention relates to the use of mercaptobenzoates for stabilising chlorine-containing polymers against thermal degradation and to the stabilised chlorine-containing polymers and novel mercaptobenzoates.

It is known that chlorine-containing polymers have to be protected from the harmful effect of light and heat, especially when being processed into preforms. A number of mercaptobenzoates and their use as stabilisers are described, for example, in U.S. Pat. Nos. 3,242,133, 4,361,665, EP-A-39 159, DE-A-1 217 609 and GB-A-936 770. A process for crosslinking halogenated polymers with the aid of alkali metal thiolates and alkaline earth metal thiolates is known from U.S. Pat. No. 4,647,629. EP-A-321 405 describes the use of mercaptobenzoates in the manufacture of organotin alkoxycarbonylphenyl mercaptides.

The present invention relates to compositions containing (a) a chlorine-containing polymer, (b) at least one Me(II) carboxylate and/or Me(II) phenolate, wherein Me(II) represents Ba, Ca, Mg, Cd, Sr or Zn, and (c) at least one compound of formula I

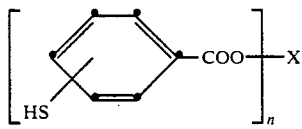

wherein n is 1, 2, 3, 4 or 6 and, when n is 1, X is $C_1$–$C_{20}$alkyl, $C_3$–$C_{20}$alkenyl, $C_5$–$C_{12}$cycloalkyl, $C_5$–$C_{12}$cycloalkyl substituted by $C_1$–$C_4$alkyl, phenyl, $C_7$–$C_9$phenylalkyl, phenyl substituted by from 1 to 3 radicals or $C_7$–$C_9$phenylalkyl substituted on the phenyl ring by from 1 to 3 radicals, the radicals being selected from the group consisting of $C_1$–$C_4$alkyl, chlorine, hydroxy, methoxy and ethoxy; when n is 2, X is $C_2$–$C_{12}$alkylene, $C_2$–$C_{12}$alkylene substituted by phenyl, or $C_2$–$C_{12}$alkylene interrupted by oxygen or sulfur atoms; when n is 3, X is a group of formula II

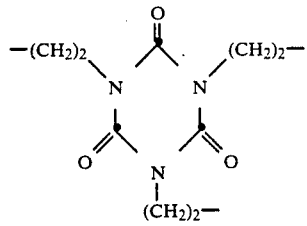

or is $C_3$–$C_7$alkanetriyl; when n is 4, X is $C_4$–$C_{10}$alkanetetrayl or a group of formula IIIa or IIIb

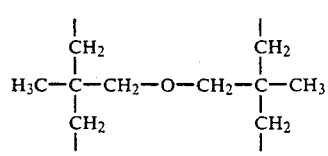

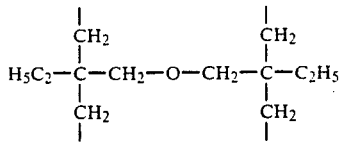

and when n is 6, X is a group of formula IV

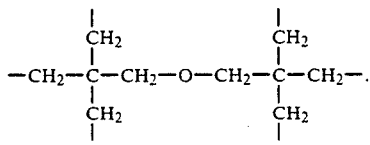

The SH group in the compounds of formula I may be in the ortho-, meta- or para-position.

$C_1$–$C_{20}$alkyl may be straight-chained or branched and is, for example, methyl, ethyl, propyl, n-butyl, isobutyl, tert-butyl, pentyl, hexyl, heptyl, n-octyl, isooctyl, isononyl, n-decyl, n-dodecyl or n-octadecyl. X is preferably $C_1$–$C_{12}$alkyl, especially $C_6$–$C_{12}$alkyl, for example 2-ethylhexyl.

$C_3$–$C_{20}$alkenyl may be straight-chained or branched and is, for example, allyl, 2-methallyl, 3-methylbut-2-enyl, 3-methylbut-3-enyl, hexenyl, decenyl, undecenyl, heptadecenyl or oleyl. Preferred meanings of X as alkenyl are allyl, methallyl and oleyl.

X as $C_5$–$C_{12}$cycloalkyl which may be unsubstituted or substituted by $C_1$–$C_4$alkyl, especially methyl, is, for example, cyclopentyl, cyclohexyl, methylcyclohexyl, 4-butylcyclohexyl, cycloheptyl, cyclooctyl or cyclododecyl. $C_5$–$C_7$cycloalkyl, especially cyclohexyl, is preferred.

$C_7$–$C_9$phenylalkyl is preferably benzyl or phenylethyl.

Phenyl substituted by from 1 to 3 radicals is, for example, o-, m- or p-chlorophenyl, 2,3-dichlorophenyl, 2,4-dichlorophenyl, 2,5-dichlorophenyl, 2,6-dichlorophenyl, 3,4-dichlorophenyl, 2,4,5-trichlorophenyl, 2,4,6-trichlorophenyl, o-, m- or p-hydroxyphenyl, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-4-tert-butylphenyl, 2-ethylphenyl, 2,6-diethylphenyl, 2,6-diethyl-4-methylphenyl, 2,6-diisopropylphenyl, 4-tert-butylphenyl, 3,5-di-tert-butyl-phenyl, 2-chloro-6-methylphenyl, 3-chloro-2-methylphenyl, 3-chloro-4-methylphenyl, 4-chloro-2-methylphenyl, 5-chloro-2-methylphenyl, 2,6-dichloro-3-methylphenyl, 2-hydroxy-4-methylphenyl, 3-hydroxy-4-methylphenyl, o-, m- or p-methoxyphenyl, o-, m- or p-ethoxyphenyl, 2,4-dimethoxyphenyl, 2,5-dimethoxyphenyl, 2,5-diethoxyphenyl, 2-methoxy-5-methylphenyl, 4-methoxy-2-methylphenyl, 3-chloro-4-methoxyphenyl, 3-chloro-6-methoxyphenyl, 3-chloro-4,6-dimethoxyphenyl or 4-chloro-2,5-dimethoxyphenyl.

$C_7$–$C_9$phenylalkyl substituted by from 1 to 3 radicals is, for example, o-, m- or p-chlorobenzyl, 2,3-dichlorobenzyl, 2,4-dichlorobenzyl, 2,5-dichlorobenzyl, 2,6-dichlorobenzyl, 3,4-dichlorobenzyl, 2,4,5-trichlorobenzyl, 2,4,6-trichlorobenzyl, o-, m- or p-hydroxybenzyl, o-, m- or p-methylbenzyl, 2,3-dimethylbenzyl, 2,4-dimethylbenzyl, 2,5-dimethylbenzyl, 2,6-dimethylbenzyl, 3,4-dimethylbenzyl, 3,5-dimethylbenzyl, 2-methyl-4-tert-butylbenzyl, 2-ethylbenzyl, 2,6-diethylbenzyl, 2,6-diethyl-4-methylbenzyl, 2,6-diisopropylbenzyl, 4-tert-butylbenzyl, 2-chloro-6-methylbenzyl, 3-chloro-2-methylbenzyl, 3-chloro-4-methylbenzyl, 4-chloro-2-methylbenzyl, 5-chloro-2-methylbenzyl, 2,6-dichloro-3-methylbenzyl, 2-hydroxy-4-methylbenzyl, 3-hydroxy-4-methylbenzyl, o-, m- or p-methoxybenzyl, o-, m- or p-ethoxybenzyl, 2,4-dimethoxybenzyl, 2,5-dimethoxybenzyl, 2,5-diethoxybenzyl, 2-methoxy-5-methylbenzyl, 4-methoxy-2-methylbenzyl, 3-chloro-4-methoxybenzyl, 3-chloro-6-methoxybenzyl, 3-chloro-4,6-dimethoxybenzyl or 4-chloro-2,5-dimethoxybenzyl.

X as $C_2$-$C_{12}$alkylene is, for example, dimethylene, trimethylene, tetramethylene, hexamethylene, 2,2-dimethyltrimethylene, 2-ethyl-2-butyltrimethylene, 2-methyl-2-propyltrimethylene, octamethylene, nonamethylene, decamethylene or dodecamethylene. $C_2$-$C_6$alkylene is preferred.

X as $C_2$-$C_{12}$alkylene substituted by phenyl is preferably 2-methyl-2-phenyltrimethylene.

X as $C_2$-$C_{12}$alkylene interrupted by, preferably up to three, oxygen or sulfur atoms is, for example, 3-thia-1,5-pentamethylene, 3,6-dithia-1,8-octamethylene, 3-oxa-1,5-pentamethylene, 4-oxa-1,7-heptamethylene or 3,6-dioxa-1,8-octamethylene. A dimethylene, trimethylene or tetramethylene group is preferably situated between the hetero atoms.

X as $C_3$-$C_7$alkanetriyl is especially

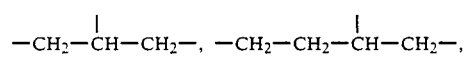

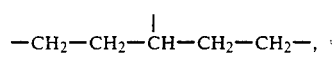

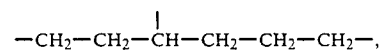

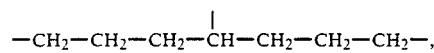

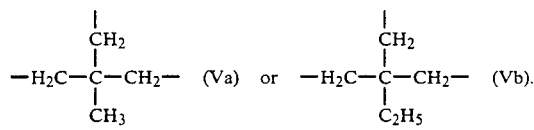

The groups Va and Vb are preferred.

X as $C_4$-$C_{10}$alkanetetrayl is especially

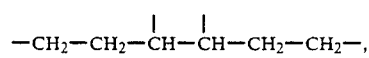

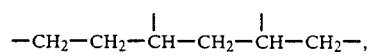

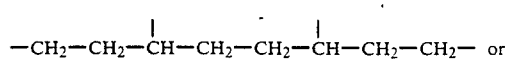

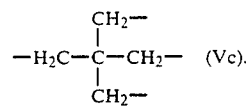

The group Vc is preferred.

Preferred compositions are those containing as component (c) a compound of formula I wherein n is 1, 2, 3 or 4 and, when n is 1, X is $C_1$-$C_{12}$alkyl, $C_3$-$C_{18}$alkenyl, $C_5$-$C_7$cycloalkyl, methyl-substituted cyclohexyl, phenyl or $C_7$-$C_9$phenylalkyl; when n is 2, X is $C_2$-$C_6$alkylene; when n is 3, X is a group of formula II or a group of formula Va or Vb

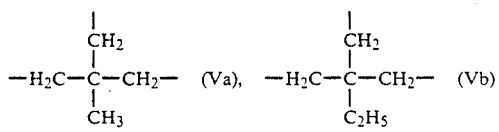

and, when n is 4, X is a group of formula Vc

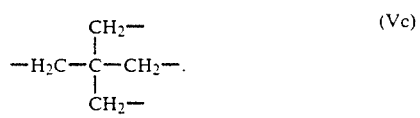

Also preferred are those compositions containing as component (c) a compound of formula I wherein n is 1, 2, 3 or 4 and, when n is 1, X is $C_1$-$C_{12}$alkyl, allyl, methallyl, oleyl, cyclohexyl, phenyl or benzyl; when n is 2, X is $C_2$-$C_6$alkylene; when n is 3, X is a group of formula Va or Vb and, when n is 4, X is a group of formula Vc.

In the compounds of formula I n is preferably 1 and X is preferably $C_1$-$C_{12}$alkyl.

The compound 2-ethylhexyl thiosalicylate or 1,6-hexamethylene bis[thiosalicylate] is especially preferred as component (c).

Component (b) is preferably a Me(II) carboxylate, wherein Me(II) represents Ba, Ca, Mg, Cd or Zn. The carboxylates are preferably salts of carboxylic acids having from 7 to 20 carbons atoms, e.g. benzoates, alkanoates or alkenoates, preferably stearates, oleates, laurates, palmitates, hydroxystearates or 2-ethylhexanoates. Stearates, oleates or p-tert-butylbenzoates are especially preferred.

Mixtures of Ba/Zn carboxylates or Ca/Zn carboxylates are also especially preferred as component (b).

If component (b) is a Me(II) phenolate, it will be especially a $C_7$-$C_{20}$alkylphenolate, for example nonylphenolate.

According to a further preference, the compositions according to the invention contain, as an additional component (d), an epoxy compound and/or a phosphite.

The epoxy compound is preferably an epoxidised oil or an epoxidised fatty acid ester, e.g. epoxidised soybean oil, epoxidised butyl oleate or epoxidised octyl oleate.

The phosphites are preferably those of the formulae

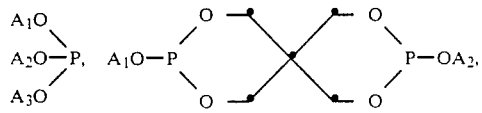

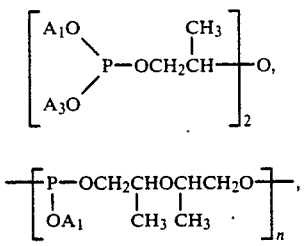

wherein each of $A_1$, $A_2$ and $A_3$, independently of the others, is $C_4-C_{18}$alkyl, $C_6-C_{18}$alkenyl, $C_5-C_7$cycloalkyl, phenyl or phenyl substituted by from one to three $C_1-C_{12}$alkyl groups.

Examples are trioctyl, tridecyl, tridodecyl, tritetradecyl, tristearyl, trioleyl, triphenyl, tricresyl, tris-p-nonylphenyl and tricyclohexyl phosphite. Preferred are aryldialkyl and alkyldiaryl phosphites, e.g. phenyldidecyl, (2,4-di-tert-butylphenyl)didodecyl, (2,6-di-tert-butylphenyl)didodecyl phosphite, and the dialkyl and diaryl pentaerythritol diphosphites, e.g. distearyl pentaerythritol diphosphite. Also preferred are the tetraphenyl- and tetraalkyl-[di-propylene glycol-1,2]diphosphites and the poly-[dipropylene glycol-1,2-phenyl phosphites] and the poly-[dipropylene glycol-1,2-alkyl phosphites].

Especially preferred organic phosphites are distearyl pentaerythritol diphosphite, tris(nonylphenyl)phosphite, phenyldidecyl phosphite, tetraphenyl-[dipropylene glycol-1,2]diphosphite and poly-[dipropylene glycol-1,2-phenyl phosphite].

The Me(II) carboxylates or Me(II) phenolates may be present in the material to be stabilised in a concentration known to one skilled in the art, for example in amounts of from 0.05 to 5% by weight.

The phosphites are used, for example, in concentrations of from 0.3 to 5, preferably from 0.5 to 1, % by weight, and the epoxy compounds, such as, for example, epoxidised soybean oil, advantageously in concentrations of from 1 to 8, preferably from 1 to 3, % by weight.

The compounds of formula I are incorporated into the chlorine-containing polymer in amounts of from 0.05 to 5, preferably from 0.05 to 1, especially from 0.1 to 0.7, % by weight.

Weight % data are based in each case on the material to be stabilised.

The chlorine-containing polymers are preferably vinyl chloride homopolymers or copolymers. Suitable comonomers for the copolymers are, for example: vinyl acetate, vinylidene chloride, transdichloroethene, ethylene, propylene, butylene, maleic acid, acrylic acid, fumaric acid, itaconic acid. Other suitable chlorine-containing polymers are post-chlorinated PVC and chlorinated polyolefins, and also graft polymers of PVC with EVA, ABS and MBS. Preferred substrates are also mixtures of the above-mentioned homopolymers and copolymers, especially vinyl chloride homopolymers, with other thermoplastic or/and elastomeric polymers, especially with ABS, MBS, NBR, SAN, EVA.

Also preferred are suspension polymers, bulk polymers and emulsion polymers.

Polyvinyl chloride is especially preferred as the chlorine-containing polymer.

Depending on the intended use of the polymers, other additives, such as, for example, phenolic antioxidants, lubricants (preferably Montan waxes or glycerol esters, fatty acid esters, paraffins, amide waxes, stearic acid, monohydroxystearic acid, dihydroxystearic acid, higher fatty alcohols), plasticisers, fillers, carbon black, asbestos, kaolin, talc, glass fibres, modifiers (such as impact resistance additives), processing aids (e.g. polymethacrylic acid esters), optical brighteners, pigments, light-stabilising agents, UV-absorbers, flame retardants or antistatic agents, may be incorporated prior to or during incorporation of the stabilisers.

Other possible additives are $\beta$-aminocrotonates, e.g. the compounds described in DE-A-804 442, DE-A-807 207 and JP-A-75/17454, pyrroles, e.g. the compounds mentioned in EP-A-22 087, aminouracils, e.g. the compounds disclosed in EP-A-65 934, aminothiouracils, e.g. the compounds known from EP-A-41 479, polyols, e.g. the compounds described in DE-A-3 019 910, $\beta$-diketones, e.g. the compounds mentioned in DE-A-2 600 516, or also mixtures of $\beta$-diketones and hydrotalcites as described e.g. in EP-A-63 180.

The incorporation of the stabiliser components into the chlorine-containing polymer is carried out most advantageously, as is usual, in a roll mill, for example a 2-roll mill, at temperatures of from 150° to 200° C. Sufficient homogenisation can generally be achieved within a period of from 5 to 15 minutes. The components can be added individually or together in the form of a pre-mix. A liquid pre-mix has proved advantageous, that is to say the operation is carried out in the presence of inert solvents and/or plasticisers.

The compounds of formula I can be prepared analogously to known processes, for example by esterification of the corresponding mercaptobenzoic acid or, when X is $C_4-C_{20}$alkyl, by transesterification of a mercaptobenzoic acid methyl ester or a mercaptobenzoic acid ethyl ester.

The invention also relates to the novel compounds of formula IA

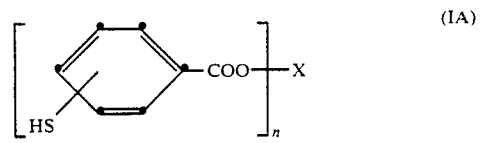

wherein n is 2, 3, 4 or 6 and, when n is 2, X is $C_2-C_{12}$alkylene substituted by phenyl or is $C_2-C_{12}$alkylene interrupted by sulfur atoms; when n is 3, X is a group of formula II

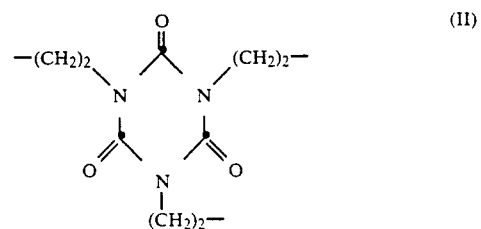

or $C_3-C_7$alkanetriyl; when n is 4, X is $C_4-C_{10}$alkanetetrayl or a group of formula IIIa or IIIb (IIIa)

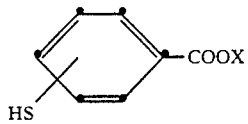

TABLE 1

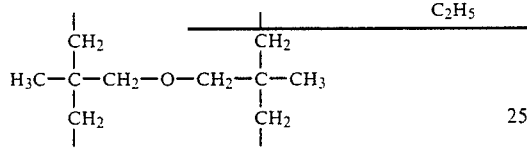

| Ex. | position of the SH group | X | refractive index $n_D^{20}$ | boiling point °C. | elemental analysis % S calculated | % S found |
|---|---|---|---|---|---|---|
| 2 | ortho | —C₂H₅ | 1.5738 | 97–98/0.8 mbar | 17.6 | 17.6 |
| 3 | ortho | iso-C₄H₉— | 1.5538 | 123/14.7 mbar | 15.3 | 15.2 |
| 4 | meta | —C₂H₅ | 1.5617 | 133/7.33 mbar | 17.6 | 17.6 |
| 5 | para | —C₂H₅ | 1.5737 | 126/4.0 mbar | 17.6 | 17.6 |
| 6 | para | —CH₂CH(CH₂)₃CH₃<br>        \|<br>       C₂H₅ | 1.5232 | — | 12.0 | 11.8 |

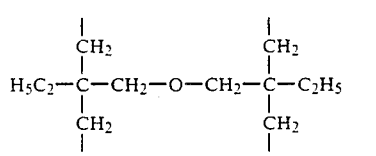

(IIIb)

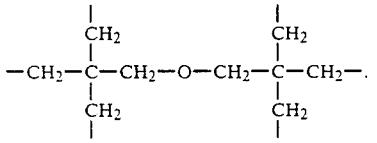

and, when n is 6, X is a group of formula IV $$\begin{array}{c} \text{CH}_2 \quad\quad \text{CH}_2 \\ | \quad\quad\quad | \\ -\text{CH}_2-\text{C}-\text{CH}_2-\text{O}-\text{CH}_2-\text{C}-\text{CH}_2-. \\ | \quad\quad\quad | \\ \text{CH}_2 \quad\quad \text{CH}_2 \\ | \quad\quad\quad | \end{array}$$ (IV)

Compounds of formula IA wherein n is 3, 4 or 6 are preferred.

The following Examples further illustrate the invention. Unless stated otherwise, parts and percentages indicated therein are by weight.

EXAMPLE 1

Preparation of 2-ethylhexyl thiosalicylate 77.1 g (0.5 mol) of thiosalicylic acid are dissolved, with stirring, in 250 ml of hot isooctanol. After the addition of 100 ml of toluene and a catalytic amount of paratoluenesulfonic acid, the reaction mixture is heated under reflux. Under azeotropic conditions, 8.5 ml of water (calculated: 9 ml) separate off after 25 hours. The residue is extracted by shaking with a bicarbonate solution, then washed with water and dried. The volatile constituents are removed in vacuo. The product is obtained after rectification with a mercury diffusion pump.

Yield: 109.7 g (=82.4% of the theoretical amount).
Boiling point: 122°–125° C. at 0.07 mbar.
Elemental analysis: Calculated: SH, 12.4%; Found: SH, 12.1%.

EXAMPLES 2–6

The compounds listed in Table 1 are prepared analogously to the process described in Example 1.

EXAMPLE 7

Preparation of phenyl thiosalicylate

In a 250 ml three-necked flask a mixture of 69.4 g (0.45 mol) of thiosalicylic acid and 42.3 g (0.45 mol) of phenol is melted at 135° C. with stirring. Then, at 125°–130° C., 24.5 g (0.16 mol) of phosphorus oxychloride are added dropwise, HCl being liberated. When the addition is complete (about 15 min.) stirring is carried out for 30 minutes. The resulting dark-brown clear solution is stirred into 500 ml of water, a brown oil separating. This oil is taken up in ethyl acetate. The organic phase is extracted three times by shaking with soda solution, washed with water, dried and concentrated to a residue. The residue, which still contains phenol, is purified by distillation. The crude product is recrystallised from 250 ml of absolute methanol in the presence of activated carbon. The product is obtained in the form of colourless crystals having a melting point of 89° C. The yield is 36.0 g (=35% of the theoretical amount).

EXAMPLE 8

Preparation of 1,6-hexamethylene bis[thiosalicylate]

In a 500 ml three-necked flask a mixture of 69.4 g (0.45 mol) of thiosalicylic acid, 17.7 g (0.15 mol) of hexanediol-1,6 and a spatula tip of paratoluenesulfonic acid is heated under reflux, with stirring, in 150 ml of xylene. Paratoluenesulfonic acid is repeatedly added during the reaction. 5.8 ml of water (calculated: 5.4 ml) separate out in the course of 10 hours. While still hot, the reaction mixture is clarified over a filtration aid and the filtrate is concentrated to a residue. The residue is taken up in ethyl acetate, extracted three times by shaking with bicarbonate solution, washed with H₂O and dried. The organic phase is again concentrated to a residue. The residue is dissolved in 350 ml of acetone in the presence of activated carbon. A light-yellow precipitate consisting of bis- and mono-ester can be precipitated from the filtrate with ice-water while stirring. The pure bisester is obtained as an almost colourless substance after extraction with methanol. The product has a melting point of 95° C.

EXAMPLE 9

Preparation of tris[thiosalicyloyloxyethyl]isocyanurate.

The preparation is analogous to that of Example 8. 0.45 mol of thiosalicylic acid and 0.1 mol of tris[hydroxyethyl]isocyanurate are used. After working up, 40.9 g of a highly viscous resin consisting of a mixture of tris- and bis-ester is obtained. The pure triester is obtained as an almost colourless substance after extraction with methanol. The product has a melting point of 91° C.

EXAMPLE 10

A dry mixture consisting of 100 parts S-PVC (®Solvic 264 GA), 3 parts epoxidised soybean oil, 0.35 parts calcium stearate, 0.15 parts zinc stearate, 0.55 parts didecyl-phenylphosphite and 0.67 parts 2-ethylhexyl thiosalicylate (Example 1) is rolled in a roll mill for 5 minutes at 180° C. Foil specimens of the 0.3 mm thick rolled sheet formed are thermally stressed at 180° C. in a drying cabinet. The Yellowness Index (YI) of the samples is determined according to ASTM D 1925 at regular intervals. The results are set forth in Table 2.

TABLE 2

| YI after stress time in minutes | | | | | | | |
|---|---|---|---|---|---|---|---|
| 0 | 5 | 10 | 15 | 20 | 25 | 30 | 35 |
| 2.4 | 3.7 | 4.2 | 5.2 | 7.7 | 8.9 | 14.6 | 23.7 |

EXAMPLE 11

A dry mixture consisting of 100 parts S-PVC (®Solvic 268 GA), 3 parts epoxidised soybean oil, 0.35 parts calcium stearate, 0.15 parts zinc stearate, 0.55 parts diisodecyl-phenylphosphite and 0.3 parts of the stabiliser indicated in Table 3 is rolled in a roll mill for 5 minutes at 180° C. Foil specimens of the 0.3 mm thick rolled sheet formed are thermally stressed at 180° C. in a test oven (®Mathis-Thermotester). The Yellowness Index (YI) of a test specimen is determined according to ASTM D 1925 at the intervals indicated. The results are set forth in Table 3.

TABLE 3

| stabiliser | YI after stress time in minutes | | | |
|---|---|---|---|---|
|  | 0 | 5 | 10 | 15 |
| compound of Example 8 | 2.8 | 3.5 | 5.3 | 9.7 |
| compound of | 3.5 | 3.2 | 3.9 | 7.1 |

TABLE 3-continued

| stabiliser | YI after stress time in minutes | | | |
|---|---|---|---|---|
|  | 0 | 5 | 10 | 15 |
| Example 9 | | | | |

EXAMPLE 12

A dry mixture consisting of 100 parts S-PVC (®Vinnol H 70 DF), 17 parts dioctyl phthalate, 3 parts epoxidised soybean oil, 0.33 parts zinc oleate, 0.53 parts barium p-(tert-butyl)benzoate, 0.7 parts diisodecyl-phenylphosphite, 0.44 parts ®SHELL SOL A (aromatic hydrocarbon mixture) and 0.2 parts of the stabiliser indicated in Tables 4a and b is rolled in a roll mill for 5 minutes at 190° C. Foil specimens of the 0.3 mm thick rolled sheet formed are tested analogously to the test method specified in Example 11. The results are set forth in Tables 4a and b.

TABLE 4a

| stabiliser | YI after stress time in minutes | | | | | | | | | | | | |
|---|---|---|---|---|---|---|---|---|---|---|---|---|---|
|  | 0 | 5 | 10 | 15 | 20 | 25 | 30 | 35 | 40 | 45 | 50 | 55 | 60 |
| none | 8.4 | 11.9 | 14.4 | 18.4 | 22.0 | 23.2 | 22.8 | 20.5 | 19.1 | 19.0 | 21.8 | 27.8 | 36.7 |
| compound of Example 1 | 0.6 | 1.3 | 1.7 | 3.0 | 6.5 | 9.6 | 12.0 | 13.3 | 13.8 | 14.8 | 15.8 | 18.4 | 25.2 |
| compound of Example 2 | 1.1 | 1.4 | 2.5 | 4.6 | 7.5 | 10.5 | 12.0 | 12.7 | 13.4 | 14.4 | 16.1 | 19.7 | 26.1 |
| compound of Example 3 | 0.9 | 1.4 | 1.9 | 3.4 | 6.7 | 9.6 | 11.3 | 12.2 | 12.8 | 13.4 | 16.6 | 17.3 | 23.2 |

TABLE 4b

| stabiliser | YI after stress time in minutes | | | | | | | | | | | | |
|---|---|---|---|---|---|---|---|---|---|---|---|---|---|
|  | 0 | 5 | 10 | 15 | 20 | 25 | 30 | 35 | 40 | 45 | 50 | 55 | 60 |
| compound of Example 8 | 2.1 | 2.4 | 3.4 | 5.5 | 7.8 | 10.1 | 11.6 | 12.4 | 13.3 | 14.1 | 15.5 | 17.8 | 22.4 |
| compound of Example 9 | 3.4 | 2.9 | 3.5 | 4.3 | 8.1 | 12.0 | 14.6 | 15.6 | 16.0 | 16.7 | 17.3 | 19.6 | 23.9 |

What is claimed is:

1. A composition containing (a) a chlorine-containing polymer selected from the group consisting of vinyl chloride polymers, a post chlorinated polyvinyl chloride polymer and chlorinated polyolefins (b) an effective stabilising amount of a Me(II) carboxylate and/or Me(II) phenolate, wherein Me(II) represents Ba, Ca, Mg, Cd, Sr or Zn, and (c) an effective stabilising amount of a compound of formula I

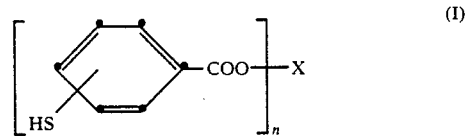

wherein n is 1, 2, 3, 4 or 6 and, when n is 1, X is $C_1$–$C_{20}$alkyl, $C_3$–$C_{20}$alkenyl, $C_5$–$C_{12}$cycloalkyl, $C_5$–$C_{12}$cycloalkyl substituted by $C_1$–$C_4$alkyl, phenyl, $C_7$–$C_9$phenylalkyl, phenyl substituted by from 1 to 3 radicals or $C_7$–$C_9$phenylalkyl substituted on the phenyl ring by from 1 to 3 radicals, the radicals being selected from the group consisting of $C_1$–$C_4$alkyl, chlorine, hydroxy, methoxy and ethoxy; when n is 2, X is $C_2$–$C_{12}$alkylene, $C_2$–$C_{12}$alkylene substituted by phenyl, or $C_2$–$C_{12}$alkylene interrupted by oxygen or sulfur atoms; when n is 3, X is a group of formula II

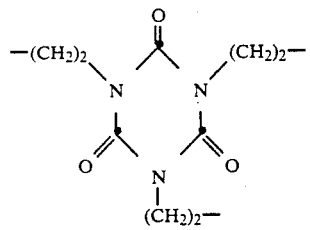

or is $C_3$-$C_7$alkanetriyl; when n is 4, X is $C_4$-$C_{10}$alkanetetrayl or a group of formula IIIa or IIIb

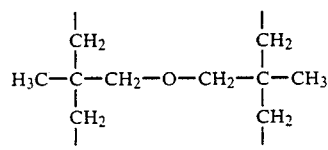

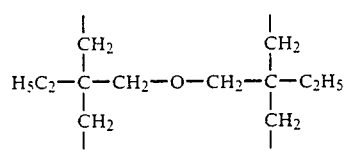

and when n is 6, X is a group of formula IV

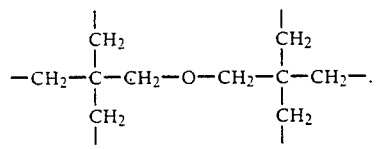

2. A composition according to claim 1, wherein n is 1, 2, 3 or 4 and, when n is 1, X is $C_1$-$C_{12}$alkyl, $C_3$-$C_{18}$alkenyl, $C_5$-$C_7$cycloalkyl, methyl-substituted cyclohexyl, phenyl or $C_7$-$C_9$phenylalkyl; when n is 2, X is $C_2$-$C_6$alkylene; when n is 3, X is a group of formula II or a group of formula Va or Vb

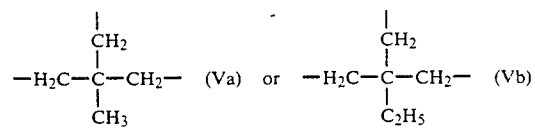

and, when n is 4, X is a group of formula Vc

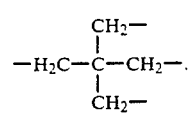

3. A composition according to claim 1 or 2, wherein n is 1, 2, 3 or 4 and, when n is 1, X is $C_1$-$C_{12}$alkyl, allyl, methallyl, oleyl, cyclohexyl, phenyl or benzyl; when n is 2, X is $C_2$-$C_6$alkylene; when n is 3, X is a group of formula Va or Vb and, when n is 4, X is a group of formula Vc.

4. A composition according to claim 1, wherein n is 1 and X is $C_1$-$C_{12}$alkyl.

5. A composition according to claim 1, wherein n is 1.

6. A composition according to claim 1, wherein the compound of formula I is 2-ethylhexyl thiosalicylate or 1,6-hexamethylene bis[thiosalicylate].

7. A composition according to claim 1, containing as component (b) at least one Me(II) carboxylate, wherein Me(II) represents Ba, Ca, Mg, Cd or Zn.

8. A composition according to claim 1, containing as component (b) a mixture of Ba/Zn carboxylates or Ca/Zn carboxylates.

9. A composition according to claim 1, containing as an additional component (d) an effective amount of an epoxy compound and/or a phosphite.

10. A composition according to claim 1, wherein the chlorine-containing polymer is polyvinyl chloride.

11. A method for stabilising a chlorine-containing polymer selected from the group consisting of vinyl chloride polymers, a post chlorinated polyvinyl chloride polymer and chlorinated polyolefins against thermal degradation, which comprises incorporating into said polymer an effective stabilising amount of a compound of formula I according to claim 1 and an effective stabilising amount of a Me(II) carboxylate and/or Me(II) phenolate, wherein Me(II) represents Ba, Ca, Mg, Cd, Sr or Zn.

12. Compounds of formula IA

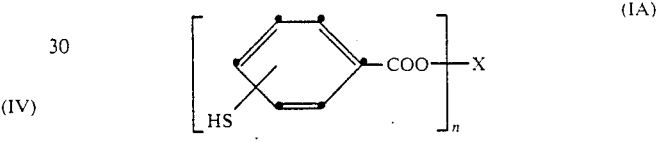

wherein n is 2, 3, 4 or 6 and, when n is 2, X is $C_2$-$C_{12}$alkylene substituted by phenyl or is $C_2$-$C_{12}$alkylene interrupted by sulfur atoms; when n is 3, X is a group of formula II

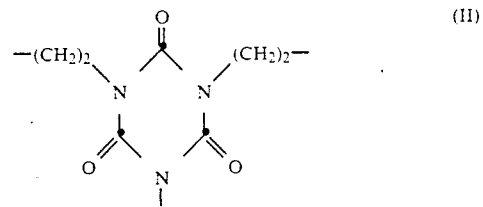

or $C_3$-$C_7$alkanetriyl; when n is 4, X is $C_4$-$C_{10}$alkanetetrayl or a group of formula IIIa or IIIb

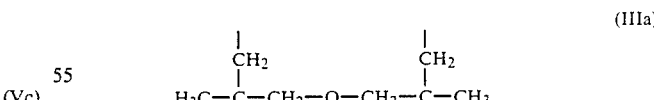

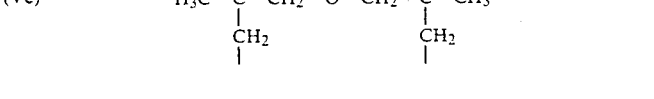

and, when n is 6, X is a group of formula IV

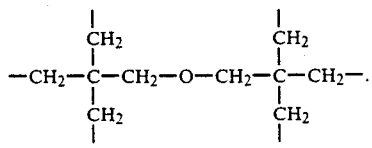 (IV)
13. Compounds according to claim 12, wherein n is 3, 4 or 6.
* * * * *
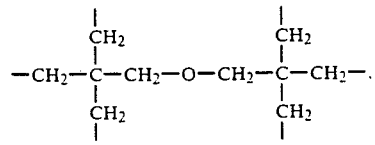 (IV)
13. Compounds according to claim 12, wherein n is 3, 4 or 6.
* * * * *